(12) United States Patent
Tanaka et al.

(10) Patent No.: US 9,962,350 B2
(45) Date of Patent: May 8, 2018

(54) AGENT FOR IMPROVING NORMAL DEVELOPMENT RATE OF FERTILIZED EGGS

(71) Applicants: SBI Pharmaceuticals Co., Ltd., Tokyo (JP); Yamagata University, Yamagata (JP)

(72) Inventors: Tohru Tanaka, Tokyo (JP); Motowo Nakajima, Tokyo (JP); Kiwamu Takahashi, Tokyo (JP); Osamu Nakajima, Yamagata (JP)

(73) Assignees: SBI Pharmaceuticals Co., Ltd., Tokyo (JP); Yamagata University, Yamagata (JP)

(*) Notice: Subject to any disclaimer, the term of this patent is extended or adjusted under 35 U.S.C. 154(b) by 0 days. days.

(21) Appl. No.: 15/320,337

(22) PCT Filed: Jul. 10, 2015

(86) PCT No.: PCT/JP2015/003515
§ 371 (c)(1),
(2) Date: Dec. 20, 2016

(87) PCT Pub. No.: WO2016/006260
PCT Pub. Date: Jan. 14, 2016

(65) Prior Publication Data
US 2017/0157074 A1 Jun. 8, 2017

(30) Foreign Application Priority Data
Jul. 11, 2014 (JP) ................. 2014-143204

(51) Int. Cl.
A61K 31/197 (2006.01)
A61K 33/26 (2006.01)
A01K 67/02 (2006.01)
A61K 45/06 (2006.01)

(52) U.S. Cl.
CPC ............ *A61K 31/197* (2013.01); *A01K 67/02* (2013.01); *A61K 33/26* (2013.01); *A61K 45/06* (2013.01)

(58) Field of Classification Search
CPC .............................. A61K 31/197; A01K 67/02
USPC ........................................................ 424/647
See application file for complete search history.

(56) References Cited

U.S. PATENT DOCUMENTS

2008/0026075 A1* 1/2008 Kondo ............... A61K 31/197
424/630

FOREIGN PATENT DOCUMENTS

| EP | 1413303 A1 | 4/2004 |
| JP | H06-189650 | 7/1994 |
| JP | H08-289779 | 11/1996 |
| JP | H09-070240 | 3/1997 |
| JP | 2001-017160 | 7/1999 |
| JP | 2002-272315 | 9/2002 |
| JP | 2003-024055 | 1/2003 |
| JP | 2010-187629 | 2/2009 |
| JP | 2011-16753 | 1/2011 |
| JP | 2012-105585 | 6/2012 |
| WO | 2006/025286 A1 | 3/2006 |
| WO | 2009/139156 A1 | 11/2009 |
| WO | 2010/050179 | 5/2010 |

OTHER PUBLICATIONS

Peña-Rosas et al., title: Daily oral iron supplementation during pregnancy, Cochrane Database Syst Rev.; vol. 12; published online Dec. 12, 2012).*
Virtus Pharmaceuticals LLC, title: Prenatal Vitamin No. 53 Iron Fum Folic Acid Docusate CA DHA- ascorbic acid, cholecalciferol, .alpha.-tocopherol, d-, pyridoxine hydrochloride, folic acid, biotin, calcium, ferrous fumarate, omega-3 fatty acids and docusate capsule, gelatin coated; published Apr. 2014.*
Akira, Shigeo et al. "In vitro fertilization and embryo transfer Present and Future" Nihon Ika Daigaku Igakkai Zasshi, vol. 66, No. 1 45-48, 1999.
Quinn, Patrick et al "Improved pregnancy rate in human in vitro fertilization with the use of a medium based on the composition of human tubal fluid" Fertility and Sterility, vol. 44, 493-498, Oct. 1985.
Wright et al., "Aspects of in Vitro Fertilization and Embryo Culture in Domestic Animals" J. Anim. Sci., 53, 702-729, 1981.

(Continued)

*Primary Examiner* — Yanzhi Zhang
(74) *Attorney, Agent, or Firm* — Edwin S. Flores; Daniel J. Chalker; Chalker Flores, LLP

(57) ABSTRACT

It is intended to provide an in vitro culture medium that allows the in vitro culture of fertilized eggs to progress normally to the blastocyst stage without arresting the development thereof. The normal development rate of a fertilized egg is improved by using 5-aminolevulinic acids represented by the following formula (I) (wherein $R^1$ represents a hydrogen atom or an acyl group, and $R^2$ represents a hydrogen atom, a linear or branched alkyl group, a cycloalkyl group, an aryl group, or an aralkyl group) or salts thereof as an agent for improving a normal development rate of a fertilized egg.

(I)

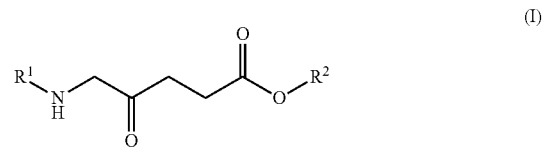

10 Claims, 7 Drawing Sheets

(56) References Cited

OTHER PUBLICATIONS

Wilt, F.H., "Heme and regulation of embryonic hemoglobin synthesis", Biochemical and Biophysical Research Communications, vol. 33, Issue 1, 113-118.
Bonkovsky, H.L., "Mechanism of iron potentiation of hepatic uroporphyria: studies in cultured chick embryo liver cells", Hepatology. Sep. 1989;10(3):354-64.
International Report on Patentability [PCT/JP2015/003515] dated Jul. 10, 2015.
Extended European Search Report [EP 15818957.1] dated Oct. 26, 2017.

\* cited by examiner

[Figure 1]
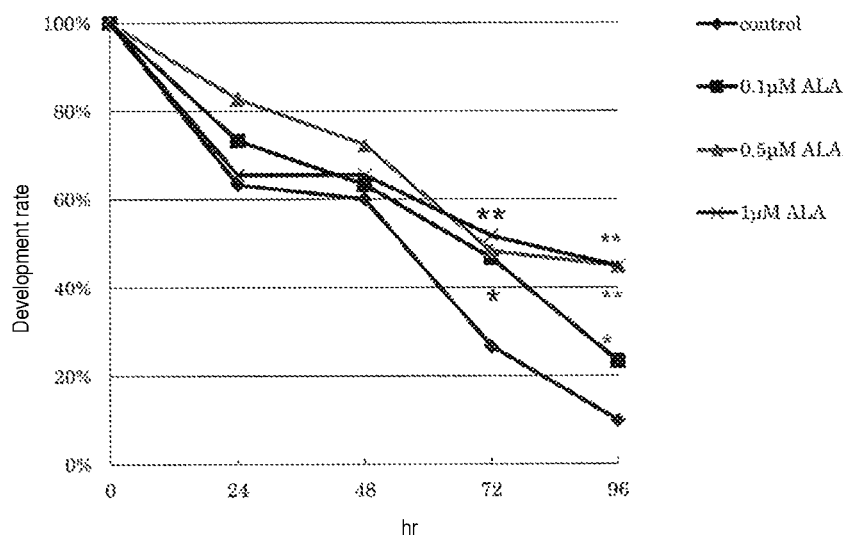
(vs control chi-square test **:p<0.01, *:p<0.05)
[Figure 2]
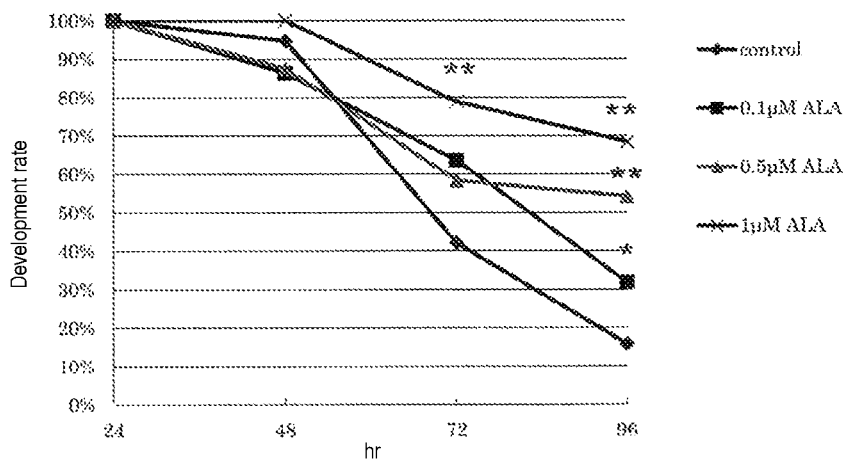
(vs control chi-square test **:p<0.01, *:p<0.05)

[Figure 3]
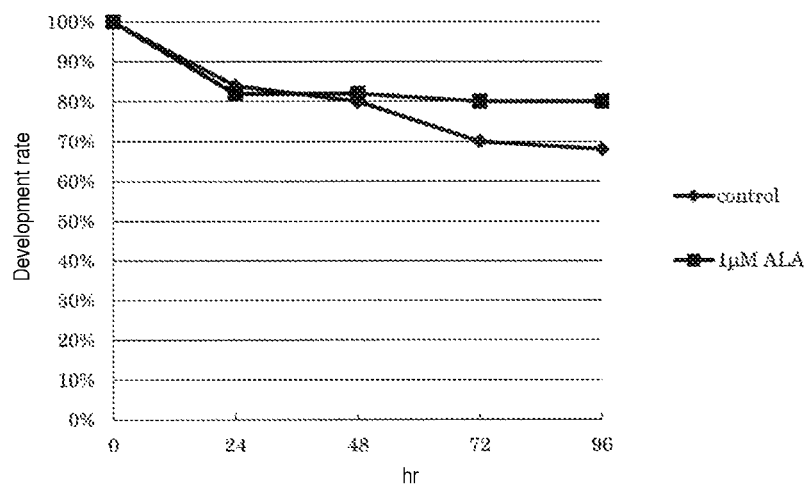
[Figure 4]
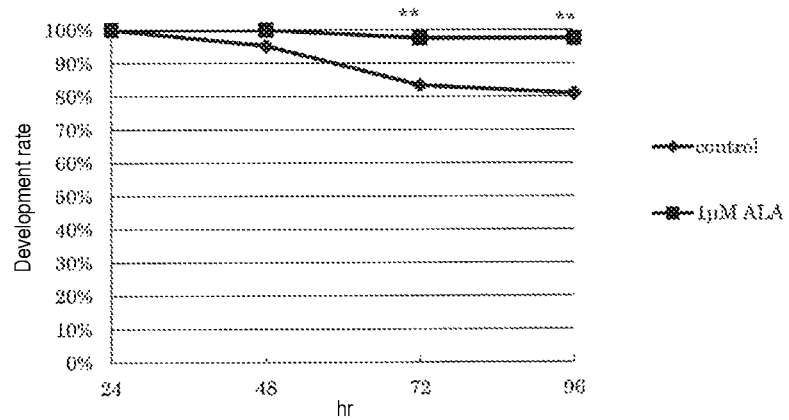
(vs control chi-square test **:p<0.01, *:p<0.05)

[Figure 5]
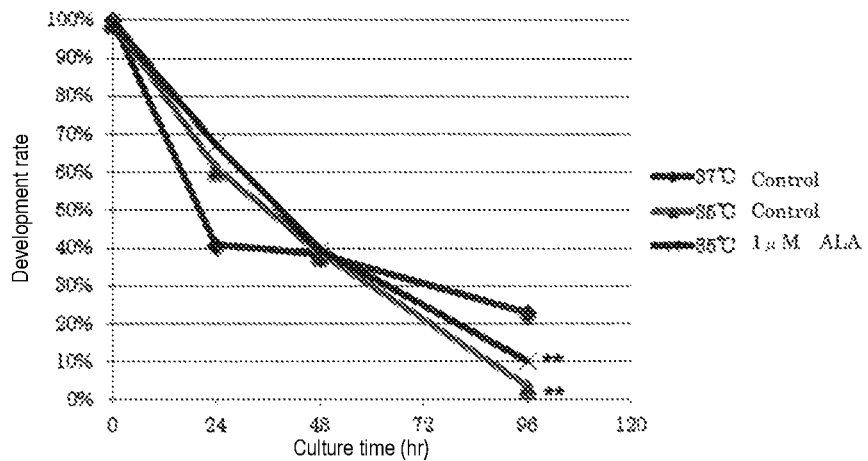
Culture time 96 hr, 37℃ Control vs 35℃ Control chi-square test p<0.01(**)
Culture time 96 hr, 35℃ Control vs 35℃ 1μM ALA chi-square test p<0.01(**)
p=0.0074
[Figure 6]
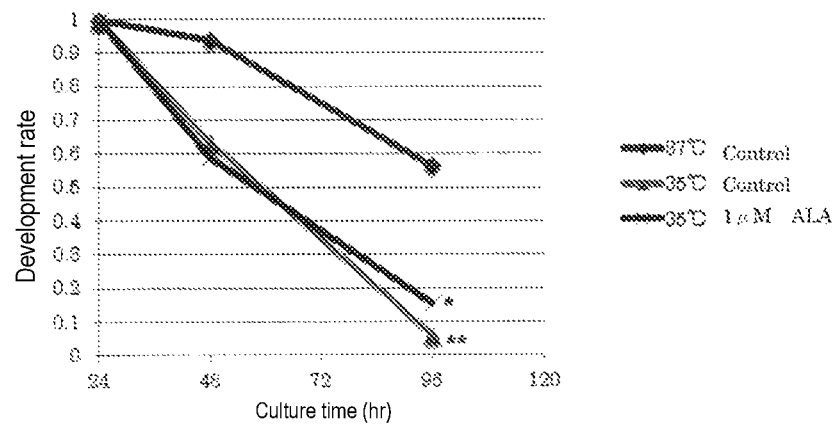
Culture time 96 hr, 37℃ Control vs 35℃ Control chi-square test p<0.01(**)
Culture time 96 hr, 35℃ Control vs 35℃ 1μM ALA chi-square test p<0.05(*)
p=0.01467

[Figure 7]
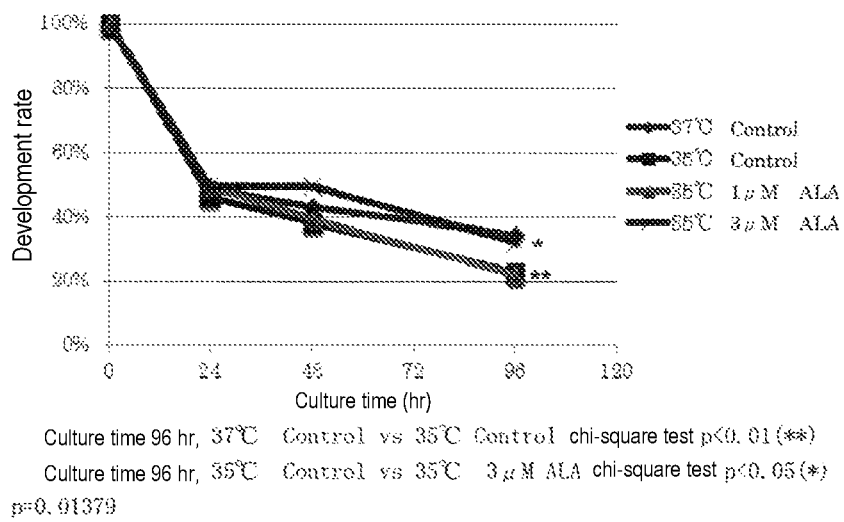
Culture time 96 hr, 37℃ Control vs 35℃ Control chi-square test p<0.01(**)
Culture time 96 hr, 35℃ Control vs 35℃ 3μM ALA chi-square test p<0.05(*)
p=0.01379
[Figure 8]
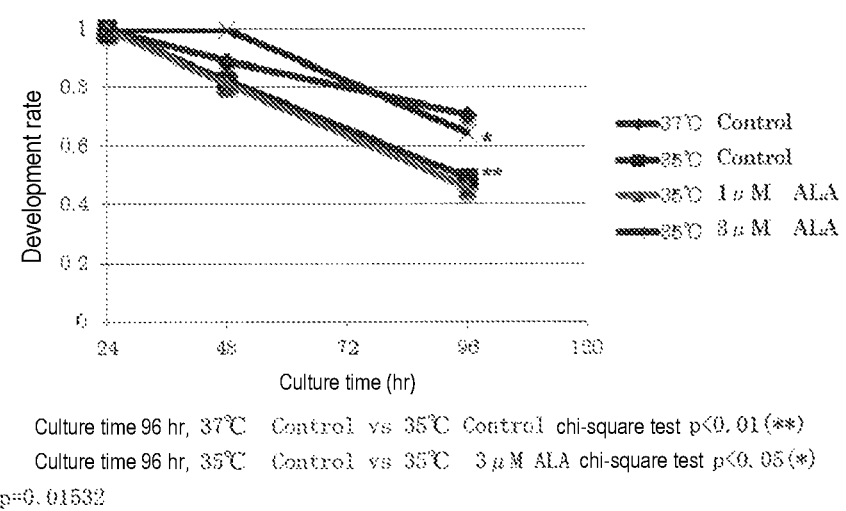
Culture time 96 hr, 37℃ Control vs 35℃ Control chi-square test p<0.01(**)
Culture time 96 hr, 35℃ Control vs 35℃ 3μM ALA chi-square test p<0.05(*)
p=0.01532

[Figure 9]
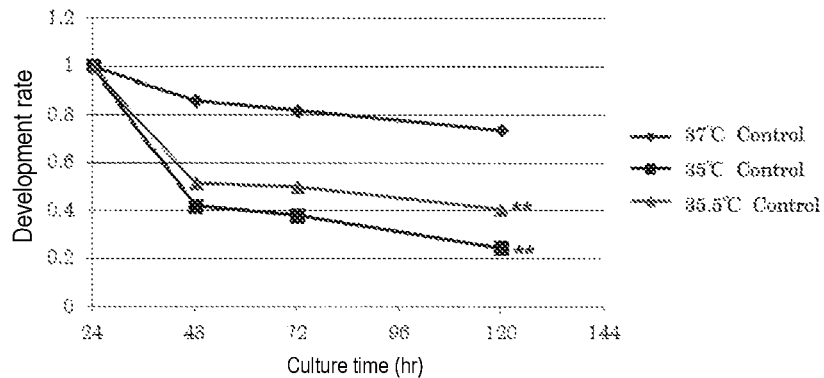
Culture time 120 hr, 37℃ Control vs 35.5℃ Control chi-square test p<0.01 (**)
Culture time 120 hr, 35℃ Control vs 35℃ Control chi-square test p<0.01(**)
[Figure 10]
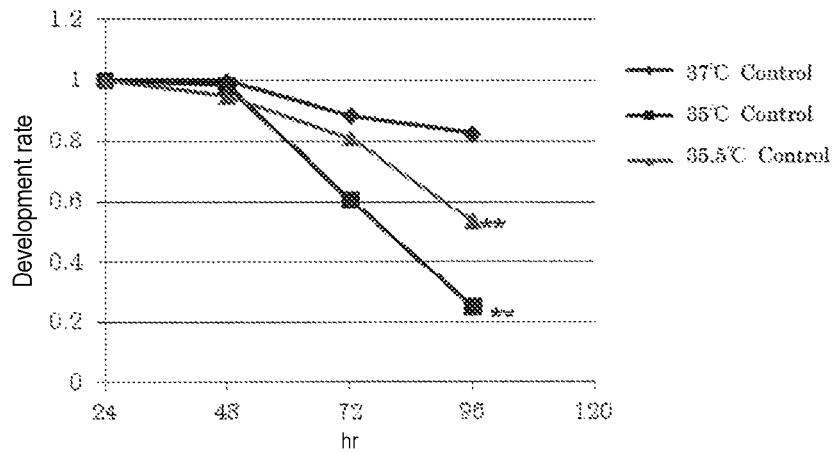
Culture time 120 hr, 37℃ Control vs 35.5℃ Control chi-square test p<0.01(**)
Culture time 120 hr, 35℃ Control vs 35℃ Control chi-square test p<0.01(**)

[Figure 11]
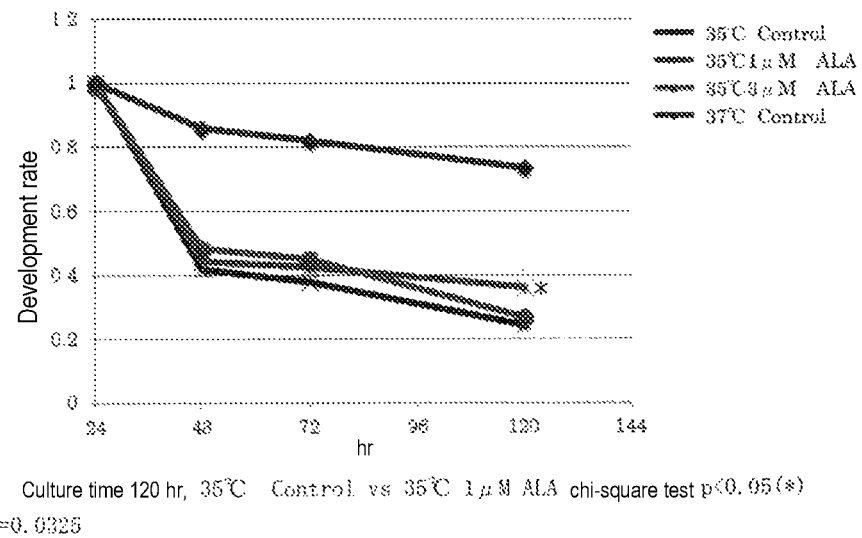
Culture time 120 hr, 35°C Control vs 35°C 1μM ALA chi-square test p<0.05(*)
p=0.0325
[Figure 12]
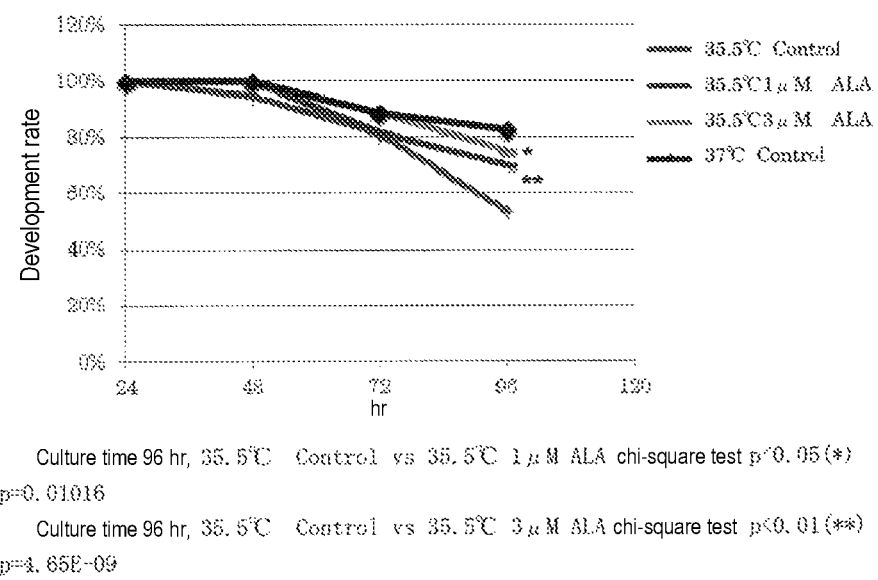
Culture time 96 hr, 35.5°C Control vs 35.5°C 1μM ALA chi-square test p<0.05(*)
p=0.01016
Culture time 96 hr, 35.5°C Control vs 35.5°C 3μM ALA chi-square test p<0.01(**)
p=4.65E-09

[Figure 13]
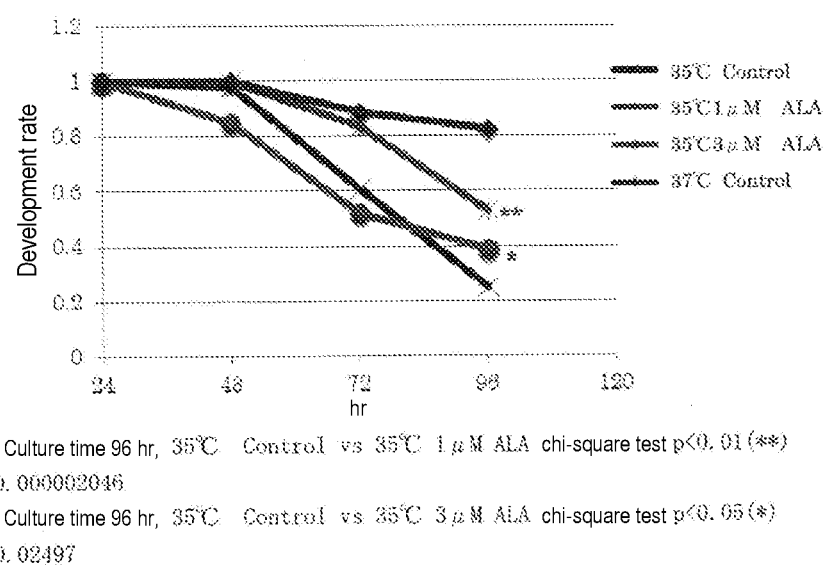
Culture time 96 hr, 35°C Control vs 35°C 1 μM ALA chi-square test p<0.01 (**)
p=0.000002046
Culture time 96 hr, 35°C Control vs 35°C 3 μM ALA chi-square test p<0.05 (*)
p=0.02497

AGENT FOR IMPROVING NORMAL DEVELOPMENT RATE OF FERTILIZED EGGS

CROSS-REFERENCE TO RELATED APPLICATIONS

This application is the National Stage of International Application No. PCT/JP2015/003515, filed on Jul. 10, 2015 claiming the priority of JP 2014-143204, filed on Jul. 11, 2014, the content of each of which is incorporated by reference herein.

TECHNICAL FIELD

The present invention relates to an agent for improving a normal development rate of a fertilized egg, comprising 5-aminolevulinic acids or salts thereof (ALAs), a kit for improving a normal development rate of a fertilized egg, a method for improving a normal development rate of a fertilized egg, comprising contacting the fertilized egg with ALAs, ALAs for use in improvement in normal development rate of fertilized eggs, and use of ALAs for preparing an agent for improving a normal development rate of fertilized eggs.

BACKGROUND ART

The technique of embryo transfer which involves inseminating eggs of female livestock having excellent genetic characters with sperms of male livestock also having excellent genetic characters, and culturing the fertilized eggs in vitro, followed by their transfer to the uterus of another female livestock (recipient) has been widely practiced as a technique of efficiently yielding superior livestock or laboratory animals. Examples of such a widely practiced technique include: in vivo fertilized egg transfer which involves transferring fertilized eggs harvested from a donor (source animal of the fertilized eggs) to a recipient (animal which receives the fertilized eggs) synchronized to induce pseudopregnancy by hormone treatment or the like, and allowing the resulting pregnant animal to give birth; and in vitro fertilized egg transfer which employs fertilized eggs in a state transferable in utero produced by isolating immature ova from the ovary of livestock after failure-no-failure confirmation of fresh, etc., obtained in a slaughterhouse, followed by the in vitro maturation, fertilization, and developmental culture of the ova.

As for humans, Dr. Edwards and Dr. Steptoe reported, in 1978, success in in vitro fertilization (IVF)-embryo transfer (ET) method which involves fertilizing ova with sperms in an in vitro culture solution, and transferring the in vitro cultured embryos in utero (see, for example, non-patent document 1). Furthermore, HTF medium (human tubal fluid medium) having composition similar to the electrolytic composition of a human oviductal fluid serving as a fertilization site has been developed as a medium for human in vitro fertilization (see, for example, non-patent document 2). This has made the beginning of studies on a medium for in vitro fertilization instead of a versatile medium previously used such as Ham's F-10 medium.

As such media for in vitro fertilization, there have been proposed, for example, a medium composition for artificial insemination containing sericin, wherein embryos harvested by in vivo artificial insemination, or embryos yielded by in vitro fertilization can be cultured (see, for example, patent document 1), a medium composition for artificial insemination containing xanthophyll (see, for example, patent document 2), a medium for the in vitro culture of pig embryos, comprising pyruvic acid or lactic acid or a salt thereof, and taurine or a precursor thereof as essential components (see, for example, patent document 3), a method for improving a development rate of fertilized mammalian eggs, comprising adding a vascular endothelial growth factor to a development medium for fertilized mammalian eggs, and coculturing the eggs with feeder cells so that the normal development rate of the fertilized eggs is enhanced (see, for example, patent document 4), an amino acid-containing medium composition for in vitro fertilization substantially free from L-glutamine or a derivative thereof capable of forming L-glutamine by hydrolysis (see, for example, patent document 5), a medium composition for in vitro fertilization usable in mammalian ovum or early embryo culture or sperm preparation or culture, containing 21 types of amino acids contained in follicular fluids, or derivatives thereof capable of forming such amino acids by hydrolysis, in free forms or in forms of pharmacologically acceptable salts thereof (see, for example, patent document 6), a serum-free medium for the in vitro culture of fertilized bovine eggs, consisting of low-glucose concentration TCM199 medium containing lactic acid or a soluble salt thereof, pyruvic acid or a soluble salt thereof, a basic fibroblast growth factor, and tumor growth factor-$\beta 1$ (see, for example, patent document 7), and a method for improving a conception rate, comprising allowing magnetic force to act on sperms of a male, ova of a female, or fertilized eggs obtained therefrom (see, for example, patent document 8).

Intracytoplasmic sperm injection (ICSI) which involves aspirating sperms into a pipette for sperm injection and injecting the sperms into the ooplasm has been further developed as one form of the IVF method. This method produces fertilized eggs at high yields even from one sperm and is therefore also effective for infertility caused by male infertility including severe oligospermia. Although the in vitro culture of fertilized eggs has become a general approach as mentioned above, it is known that the development of the cultured fertilized eggs falls short of the blastocyst stage and is arrested before the morula stage at high rates. As pointed out, this might be because some factor causes the arrest of early development, though the mechanism has yet been unknown. In the case of, for example, humans, the pregnancy rate of in vitro fertilization is approximately 20 to 25% of the total in vitro fertilization number, and only 5 to 15% thereof reportedly arrives at birth. It has also been reported as to cattle that in the in vitro culture of fertilized eggs, the development thereof is often arrested at the 8-cell stage to the 16-cell stage (see, for example, non-patent document 3).

Meanwhile, 5-aminolevulinic acid (5-ALA) is known as an intermediate of the tetrapyrrole biosynthesis pathway widely found in animals, plants, and fungi, and is generally biosynthesized from succinyl CoA and glycine by 5-aminolevulinic acid synthase. Photodynamic therapy using 5-ALA (ALA-PDT) has also been developed and has received attention as a treatment method that is low invasive and maintains QOL. For example, diagnostic or therapeutic agents for tumors using ALA or the like have been reported. In addition, 5-ALA is also known to be useful as a prophylactic or ameliorating agent or a therapeutic agent for adult-onset diseases, cancers, and male infertility (see, for example, patent documents 9 to 11).

PRIOR ART DOCUMENTS

Patent Documents

Patent Document 1: Japanese unexamined Patent Application Publication No. 2012-105585
Patent Document 2: Japanese unexamined Patent Application Publication No. 2010-187629
Patent Document 3: Japanese unexamined Patent Application Publication No. 2003-024055
Patent Document 4: Japanese unexamined Patent Application Publication No. 2002-272315
Patent Document 5: Japanese unexamined Patent Application Publication No. 2001-017160
Patent Document 6: Japanese unexamined Patent Application Publication No. 09-070240
Patent Document 7: Japanese unexamined Patent Application Publication No. 08-289779
Patent Document 8: Japanese unexamined Patent Application Publication No. 06-189650
Patent Document 9: International Publication No. WO2010/050179
Patent Document 10: Japanese unexamined Patent Application Publication No. 2011-16753
Patent Document 11: International Publication No. WO2009/139156

Non-Patent Documents

Non-patent Document 1: Journal of Nippon Medical School, Vol. 66, No. 1, p. 45-48
Non-patent Document 2: Quinn, P. J. et al., Fertility and Sterility, 44, 493-498, 1985
Non-patent Document 3: Wright et al., J. Anim. Sci., 53, 702-729, 1981

SUMMARY OF THE INVENTION

Object to be Solved by the Invention

An object of the present invention is to provide an in vitro culture medium that allows the in vitro culture of fertilized eggs to progress normally to the blastocyst stage without arresting the development thereof.

Means to Solve the Object

The present inventors have conducted studies using various medium components to attain the object. Meanwhile, the present inventors have actually carried out the in vitro culture of fertilized mouse eggs in an in vitro culture medium supplemented with 5-ALA and consequently completed the present invention by finding that the normal development rate of fertilized eggs is thereby improved.

Specifically, the present invention is specified by the following items:
(1) an agent for improving a normal development rate of a fertilized egg, comprising a compound represented by the following formula (I) or a salt thereof:

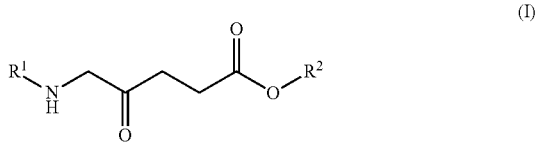
(I)

(wherein $R^1$ represents a hydrogen atom or an acyl group, and $R^2$ represents a hydrogen atom, a linear or branched alkyl group, a cycloalkyl group, an aryl group, or an aralkyl group);
(2) the agent for improving a normal development rate of a fertilized egg according to (1), wherein each of $R^1$ and $R^2$ is a hydrogen atom;
(3) the agent for improving a normal development rate of a fertilized egg according to (1) or (2), further comprising an iron compound;
(4) the agent for improving a normal development rate of a fertilized egg according to (3), wherein the iron compound is one or more compounds selected from ferric chloride, iron sesquioxide, iron sulfate, ferrous pyrophosphate, ferrous citrate, iron sodium citrate, sodium ferrous citrate, iron ammonium citrate, ferric pyrophosphate, iron lactate, ferrous gluconate, iron sodium diethylenetriaminepentaacetate, iron ammonium diethylenetriaminepentaacetate, iron sodium ethylenediaminetetraacetate, iron ammonium ethylenediaminetetraacetate, iron sodium dicarboxymethylglutamate, iron ammonium dicarboxymethylglutamate, ferrous fumarate, iron acetate, iron oxalate, ferrous succinate, sodium iron succinate citrate, heme iron, iron dextran, iron triethylenetetramine, lactoferrin iron, transferrin iron, sodium iron chlorophyllin, ferritin iron, saccharated iron oxide, and iron glycine sulfide;
(5) the agent for improving a normal development rate of a fertilized egg according to any one of (1) to (4), wherein the agent is capable of enhancing a conception rate;
(6) the agent for improving a normal development rate of a fertilized egg according to any one of (1) to (5), wherein the fertilized egg is a fertilized egg obtained by in vitro fertilization or in vivo fertilization;
(7) the agent for improving a normal development rate of a fertilized egg according to any one of (1) to (6), wherein the agent is a medium for improvement in fertilized egg development rate further comprising an in vitro culture medium for fertilized mammalian eggs;
(8) a method for improving a normal development rate of a fertilized egg, comprising contacting the fertilized egg with an agent for improving a normal development rate of a fertilized egg according to any one of (1) to (7);
(9) a method for improving a normal development rate of a fertilized egg, comprising administering an agent for improving a normal development rate of a fertilized egg according to any one of (1) to (7) to a female parent subject;
(10) a kit for improving a normal development rate of a fertilized egg comprising: a) a compound represented by the formula (I) or a salt thereof; and b) an iron compound;
(11) the kit for improving a normal development rate of a fertilized egg according to (10), further comprising c) an in vitro culture medium for fertilized mammalian eggs;
(12) use of a compound represented by the formula (I) or a salt thereof for preparing an agent for improving a normal development rate of a fertilized egg;
(13) the use according to (12), wherein the compound represented by the formula (I) or a salt thereof is used with an iron compound;
(14) the use according to (13), wherein the compound represented by the formula (I) or a salt thereof and the iron compound are used with an in vitro culture medium for fertilized mammalian eggs; and
(15) a compound represented by the formula (I) or a salt thereof for use in improvement in normal development rate of a fertilized egg.

EFFECT OF THE INVENTION

The present invention can improve a development rate or a conception rate for artificial insemination and a conception rate for spontaneous pregnancy in humans or livestock and can enhance productivity and the efficiency of breed improvement in livestock breeding.

BRIEF DESCRIPTION OF DRAWINGS

FIG. 1 is a diagram showing, in a graph form, the development rate of fertilized eggs of the C57BL/6J lineage, wherein the number of embryos whose development progressed normally was counted at each stage and the number of the fertilized eggs at 0 hours was defined as 100%.

FIG. 2 is a diagram showing, in a graph form, the development rate of fertilized eggs of the C57BL/6J lineage, wherein the number of embryos whose development progressed normally was counted at each stage and the number of 2-cell eggs 24 hours after the start of the culture of the fertilized eggs was defined as 100%.

FIG. 3 is a diagram showing, in a graph form, the development rate of fertilized eggs obtained by the mating between female mice of the BDF2 lineage and male mice of the BDF1 lineage, wherein the number of the fertilized eggs at 0 hours was defined as 100%.

FIG. 4 is a diagram showing, in a graph form, the development rate of fertilized eggs obtained by the mating between female mice of the BDF2 lineage and male mice of the BDF1 lineage, wherein the number of embryos whose development progressed normally was counted at each stage and the number of 2-cell eggs 24 hours after the start of the culture of the fertilized eggs was defined as 100%.

FIG. 5 is a diagram showing, in a graph form, time-dependent change in development rate (natural mating-derived fertilized eggs) when the number of the fertilized eggs (0 hours) in KSOM was defined as 100%.

FIG. 6 is a diagram showing, in a graph form, time-dependent change in development rate (natural mating-derived fertilized eggs) when the number of 2-cell embryos 24 hours postfertilization in KSOM was defined as 100%.

FIG. 7 is a diagram showing, in a graph form, time-dependent change in development rate (natural mating-derived fertilized eggs) when the number of the fertilized eggs (0 hours) in mWM was defined as 100%.

FIG. 8 is a diagram showing, in a graph form, time-dependent change in development rate (natural mating-derived fertilized eggs) when the number of 2-cell embryos 24 hours postfertilization in mWM was defined as 100%.

FIG. 9 is a diagram showing, in a graph form, the influence of a culture temperature on a development rate (in vitro fertilized eggs) when the number of 2-cell embryos 24 hours postfertilization in KSOM was defined as 100%.

FIG. 10 is a diagram showing, in a graph form, the influence of a culture temperature on a development rate (in vitro fertilized eggs) when the number of 2-cell embryos 24 hours postfertilization in mWM was defined as 100%.

FIG. 11 is a diagram showing, in a graph form, time-dependent change in development rate (in vitro fertilized eggs) when the number of 2-cell embryos 24 hours postfertilization in 35° C. culture in KSOM was defined as 100%.

FIG. 12 is a diagram showing, in a graph form, time-dependent change in development rate (in vitro fertilized eggs) when the number of 2-cell embryos 24 hours postfertilization in 35.5° C. culture in mWM was defined as 100%.

FIG. 13 is a diagram showing, in a graph form, time-dependent change in development rate (in vitro fertilized eggs) when the number of 2-cell embryos 24 hours postfertilization in 35° C. culture in mWM was defined as 100%.

MODE OF CARRYING OUT THE INVENTION

The agent for improving a normal development rate of a fertilized egg according to the present invention is not particularly limited as long as the agent comprises a compound represented by the formula (I) or a salt thereof (hereinafter, these are also collectively referred to as "ALAs"). The agent can also be used as a medium for improvement in fertilized egg development rate suitable for artificial insemination, comprising an in vitro culture medium for fertilized mammalian eggs. Preferably, the agent contains an iron compound in addition to ALAs. Also preferably, the agent is capable of enhancing a conception rate. The organism species from which the fertilized egg according to the present invention is derived is preferably a mammal. Examples thereof can include a human, a monkey, a mouse, a rat, a hamster, a guinea pig, cattle, a pig, a horse, a rabbit, sheep, a goat, a cat, and a dog.

Among ALAs described above, preferred examples thereof can include 5-ALA in which each of $R^1$ and $R^2$ in the formula (I) is a hydrogen atom, and a salt thereof. 5-ALA is an amino acid also called δ-aminolevulinic acid. Examples of a 5-ALA derivative can include a compound of the formula (I), other than 5-ALA, wherein $R^1$ is a hydrogen atom or an acyl group, and $R^2$ is a hydrogen atom, a linear or branched alkyl group, a cycloalkyl group, an aryl group, or an aralkyl group.

Examples of the acyl group in the formula (I) can include: a linear or branched alkanoyl group having 1 to 8 carbon atoms, such as a formyl group, an acetyl group, a propionyl group, a butyryl group, an isobutyryl group, a valeryl group, an isovaleryl group, a pivaloyl group, a hexanoyl group, an octanoyl group, and a benzylcarbonyl group; and an aroyl group having 7 to 14 carbon atoms, such as a benzoyl group, a 1-naphthoyl group, and a 2-naphthoyl group.

Examples of the alkyl group in the formula (I) can include a linear or branched alkyl group having 1 to 8 carbon atoms, such as a methyl group, an ethyl group, a propyl group, an isopropyl group, a butyl group, an isobutyl group, a sec-butyl group, a tert-butyl group, a pentyl group, an isopentyl group, a neopentyl group, a hexyl group, a heptyl group, and an octyl group.

Examples of the cycloalkyl group in the formula (I) can include a cycloalkyl group having 3 to 8 carbon atoms and optionally having a saturated or partially unsaturated bond, such as a cyclopropyl group, a cyclobutyl group, a cyclopentyl group, a cyclohexyl group, a cycloheptyl group, a cyclooctyl group, a cyclododecyl group, and a 1-cyclohexenyl group.

Examples of the aryl group in the formula (I) can include an aryl group having 6 to 14 carbon atoms, such as a phenyl group, a naphthyl group, an anthryl group, and a phenanthryl group.

Examples of the aryl moiety of the aralkyl group in the formula (I) can include the same as the aryl group described above, and examples of the alkyl moiety thereof can include the same as the alkyl group described above. Specific examples thereof can include an aralkyl group having 7 to 15 carbon atoms, such as a benzyl group, a phenethyl group, a phenylpropyl group, a phenylbutyl group, a benzhydryl group, a trityl group, a naphthylmethyl group, and a naphthylethyl group.

The 5-ALA derivative is preferably a compound in which $R^1$ is a formyl group, an acetyl group, a propionyl group, a butyryl group, or the like, or a compound in which $R^2$ is a methyl group, an ethyl group, a propyl group, a butyl group, a pentyl group, or the like. Preferred examples of the combination of $R^1$ and $R^2$ can include a combination of formyl and methyl, a combination of acetyl and methyl, a combination of propionyl and methyl, a combination of butyryl and methyl, a combination of formyl and ethyl, a combination of acetyl and ethyl, a combination of propionyl and ethyl, and a combination of butyryl and ethyl.

ALAs need only to act as an active ingredient in the form of 5-ALA of the formula (I) or a derivative thereof in vivo and can be administered, according to a dosage form, as various salts for enhancing solubility or as esters serving as prodrugs (precursors) that are decomposed by in vivo enzymes. Examples of the salt of 5-ALA or the derivative thereof can include a pharmacologically acceptable acid-addition salt, metal salt, ammonium salt, and organic amine-addition salt. Examples of the acid-addition salt can include: each inorganic acid salt such as hydrochloride, hydrobromide, hydroiodide, phosphate, nitrate, and sulfate; and each organic acid-addition salt such as formate, acetate, propionate, toluenesulfonate, succinate, oxalate, lactate, tartrate, glycolate, methanesulfonate, butyrate, valerate, citrate, fumarate, maleate, and malate. Examples of the metal salt can include: each alkali metal salt such as a lithium salt, a sodium salt, and a potassium salt; each alkaline earth metal salt such as a magnesium and a calcium salt; each salt of a metal such as aluminum and zinc. Examples of the ammonium salt can include ammonium salt and an alkylammonium salt such as tetramethylammonium salt. Examples of the organic amine salt can include each salt such as triethylamine salt, piperidine salt, morpholine salt, and toluidine salt. These salts can also be used as solutions upon application.

Among these ALAs, desirable ones are 5-ALA and various esters thereof such as 5-ALA methyl ester, 5-ALA ethyl ester, 5-ALA propyl ester, 5-ALA butyl ester, and 5-ALA pentyl ester, as well as hydrochlorides, phosphates, and sulfates of 5-ALA or the esters thereof. Particularly preferred examples thereof can include 5-ALA hydrochloride and 5-ALA phosphate.

These ALAs can be produced by any method known in the art such as chemical synthesis, microbial production, or enzymatic production. Also, these ALAs can form hydrates or solvates. Any one of these ALAs can be used alone, or two or more thereof can be used in appropriate combination.

The iron compound can be an organic salt or an inorganic salt. Examples of the inorganic salt can include ferric chloride, iron sesquioxide, iron sulfate, and ferrous pyrophosphate. Examples of the organic salt can include: an organic acid salt including a carboxylate, for example, a citrate such as ferrous citrate, iron sodium citrate, sodium ferrous citrate, and iron ammonium citrate, which are hydroxycarboxylates, ferric pyrophosphate, iron lactate, ferrous gluconate, iron sodium diethylenetriaminepentaacetate, iron ammonium diethylenetriaminepentaacetate, iron sodium ethylenediaminetetraacetate, iron ammonium ethylenediaminetetraacetate, iron sodium dicarboxymethylglutamate, iron ammonium dicarboxymethylglutamate, ferrous fumarate, iron acetate, iron oxalate, ferrous succinate, and sodium iron succinate citrate; and others such as heme iron, iron dextran, iron triethylenetetramine, lactoferrin iron, transferrin iron, sodium iron chlorophyllin, ferritin iron, saccharated iron oxide, and iron glycine sulfide. Among them, sodium ferrous citrate or iron sodium citrate is preferred.

These iron compounds can each be used alone or can be used as a mixture of two or more thereof. The amount of the iron compound used (the amount of the iron compound added or the dose thereof) can be 0.01 to 100 times and is desirably 0.05 times to 10 times, more preferably 0.1 times to 8 times, as a molar ratio with respect to the dose of ALAs (in terms of the amount of 5-ALA).

The agent for improving a normal development rate of a fertilized egg, comprising ALAs and the iron compound in combination according to the present invention can be used as a composition containing ALAs and the iron compound, or these components can also be used each alone at the same time or in a staggered manner. In the case of using these components each alone, the components are preferably used at the same time. In the case of using these components each alone in a staggered manner, the components are preferably used such that the administration of ALAs and the iron compound can exert additive effects, preferably synergistic effects.

In the present invention, the fertilized egg refers to a single cell that has been formed by fertilization (i.e., a sperm enters the ovum so that the nucleus of the sperm fuses with the nucleus of the ovum) and is able to grow by somatic cell division. Examples of a method for obtaining the fertilized egg can include a method of ex vivo harvest of in vivo fertilized eggs (ovum collection), a method of obtaining fertilized eggs by in vitro fertilization, and a method of freeze-drying the fertilized eggs obtained by these methods and using them after thawing.

Examples of the in vivo fertilization can include in vivo fertilization that is performed in such a way that nearly matured ovum released (ovulated) from the ovary enters the oviduct and meets a sperm on the way to travelling down the oviduct while the maturation is pursued. In the case of a mouse, examples of a method for obtaining the in vivo fertilized eggs can include a method which involves euthanizing a mouse having fertilized eggs by an appropriate method, isolating the oviduct by a routine method, cutting up the ampulla of the oviduct with an injection needle, and removing cumulus cells by the hyaluronidase treatment of a mass of fertilized eggs to obtain the fertilized eggs.

Examples of the in vitro fertilization can include the artificial in vitro practice of the fertilization described above. Examples of the in vitro fertilization method can include a microinsemination method such as a method that is performed by coculturing ex vivo isolated ova with sperms, assisted hatching, subzonal insemination, and intracytoplasmic sperm injection (ICSI). Among them, preferred examples thereof can include ICSI which involves injecting a sperm into the cytoplasm of the ovum using an ultrathin pipette under a microscope.

Examples of the ovum for use in the in vitro fertilization can include ovulated ovum or intrafollicular ovum matured to be nearly ovulated, ovum collected by ex vivo harvest, mature cultured ovum obtained by maturing ex vivo harvested immature ovum by a routine culture method, and ovum thawed after cryopreservation thereof. Examples of a method for the ex vivo harvest of intrafollicular ovum can include a syringe suction method which involves stabbing an injection needle to the follicle and aspirating the ovum, a small follicle incision method which involves scraping out the contents of the follicle after incision, and an ovary slicing method which involves slicing the surface of the ovary. In the case of, for example, a pig, in vivo matured ovum obtained by superovulation through the administration of a hormone such as prostaglandin F2α, cloprostenol, or chorionic gonadotropin, as well as an in vitro matured form of the ovum harvested from the slaughterhouse-derived ovary can be used, and in vivo matured ovum, particularly, in vivo matured ovum harvested from a sexually matured (6 months or more old) female pig, is preferred. Such in vivo matured ovum can be harvested by the oviduct perfusion of the uterus and the ovary (which are obtained by superovulation) of a female pig using a PBS solution or the like. For cumulus cell-attached ovum, it is preferred to remove the cumulus cells by hyaluronidase treatment.

Examples of the sperm for use in the in vitro fertilization can include a sperm obtained by sperm collection, testicular sperm extraction, microsurgical epididymal sperm aspiration, percutaneous epididymal sperm aspiration, sperm concentration and washing, or the like, a sperm obtained by the preculture of the sperm, and a sperm thawed after cryopreservation thereof.

In the present invention, examples of the probability that fertilized eggs develop normally (normal development rate) can include the percentage at which the fertilized eggs are sequentially converted to embryos at each stage, i.e., 2-cell embryos, preferably 4-cell embryos, more preferably 8-cell embryos, further preferably morulae, particularly preferably blastocysts (blastocyst-stage embryos), by in vivo or in vitro somatic cell division without arresting the cell division and without causing cleavage different from a usually scheduled segmentation form well known to those skilled in the art. In the present invention, the improvement in normal development rate refers to improvement in normal development rate to at least 8-cell or later embryos. The morulae refer to embryos each having approximately 16 to cells which can individually be confirmed, albeit increase in cell count. The blastocysts refer to embryos having a structure divided into a trophectoderm (TE) and an inner cell mass (ICM) by forming a blastocoel. In the case of spontaneous pregnancy, the blastocysts are embryos corresponding to a structure before implantation to the lining of the uterus (in vivo developed embryo). In the case of in vitro fertilization as well, the transfer of embryos normally developed into blastocysts (in vitro developed embryo) reportedly enhances a conception rate. However, the time of the embryo transfer is not limited to the blastocyst stage. As mentioned above, the development includes in vitro development (in vitro culture) which causes in vitro somatic cell division of fertilized eggs, and in vivo development which causes in vivo somatic cell division of fertilized eggs. Thus, the combination of fertilization and development is 4 combinations: in vivo fertilization-in vitro development, in vivo fertilization-in vivo development, in vitro fertilization-in vivo development, and in vitro fertilization-in vitro development.

Examples of a method for improving a normal development rate for in vitro development using the agent for improving a normal development rate of a fertilized egg according to the present invention can include a method comprising contacting the fertilized egg with the agent for improving a normal development rate, preferably, a method comprising incubating the fertilized egg in a medium for improvement in fertilized egg development rate, comprising ALAs and an iron compound, as an in vitro culture medium for fertilized mammalian eggs, as well as a method comprising adding the agent for improving a normal development rate to a culture medium for the in vitro maturation of collected ova, and a method comprising adding the agent for improving a normal development rate to a cryopreservative agent for ova. Examples of a method for improving a normal development rate for in vivo development using the agent for improving a normal development rate of a fertilized egg according to the present invention can include a method comprising orally, sublingually, subcutaneously, intravenously, intramuscularly, nasally, intrafollicularly, or intravaginally administering the agent for improving a normal development rate to a female parent of a human or a nonhuman animal from which the ova are derived. Use of the agent for improving a normal development rate according to the present invention significantly improves the normal development rate of fertilized eggs and by extension, significantly improves a conception rate, as compared with the case of not using the agent for improving a normal development rate of a fertilized egg according to the present invention.

The in vitro culture medium for fertilized mammalian eggs that is used when the agent for improving a normal development rate of a fertilized egg according to the present invention is a medium for improvement in fertilized egg development rate is not particularly limited as long as the fertilized mammalian eggs can be cultured in the medium. Examples thereof can include HTF medium, m-HTF medium, Ham's medium, Ham's F-10 medium, MEM medium, 199 medium, BME medium, CMRL1066 medium, McCoy's 5A medium, Weymouth medium, Trowell's T-8 medium, Leibovitz's L-15 medium, NCTC medium, William's E medium, Kane and Foote medium, Brinster medium, m-Tyrode's medium, BWW medium, WK Whitten medium, TYH medium, Hoppes & Pitts medium, m-KRB medium, BO medium, T6 medium, GPM medium, KSOM, HECM medium, and a modified medium thereof. Alternatively, a commercially available dedicated medium for in vitro fertilization, such as CARD MEDIUM medium for mouse in vitro fertilization or a pig culture medium for embryo development (PZM-5) (manufactured by Research Institute for the Functional Peptides Co., Ltd.), can also be used. Specifically, preferred examples thereof can include a medium containing NaCl, KCl, $KH_2PO_4$, $MgSO_4 \cdot 7H_2O$, $NaHCO_3$, calcium lactate, sodium pyruvate, glucose, and BSA. Particularly preferred examples thereof can include M16 medium shown in Table 1 below, which is a synthetic medium most frequently used in experiments of recovering and manipulating fertilized mouse eggs.

TABLE 1

| Composition of M16 medium | | |
|---|---|---|
| Component | Concentration | Distributor |
| NaCl | 5.98 g/L (102 mM) | manufactured by Wako Pure Chemical Industries, Ltd. |
| KCl | 0.356 g/L (4.78 mM) | manufactured by Wako Pure Chemical Industries, Ltd. |
| $KH_2PO_4$ | 0.163 g/L (1.20 mM) | manufactured by Wako Pure Chemical Industries, Ltd. |
| $MgSO_4 \cdot 7H_2O$ | 0.294 g/L (1.19 mM) | manufactured by Wako Pure Chemical Industries, Ltd. |
| $NaHCO_3$ | 1.9 g/L (22.62 mM) | manufactured by Wako Pure Chemical Industries, Ltd. |
| Calcium DL-lactate pentahydrate | 0.528 g/L (1.71 mM) | manufactured by Wako Pure Chemical Industries, Ltd. |
| Sodium pyruvate | 0.025 g/L (0.23 mM) | manufactured by Sigma-Aldrich Corp. |
| Glucose | 1 g/L (5.55 mM) | manufactured by Wako Pure Chemical Industries, Ltd. |
| BSA | 3 g/L | manufactured by Sigma-Aldrich Corp. |
| Penicillin | 100 IU/mL | Manufactured by Thermo Fisher Scientific Inc. (Gibco) |

TABLE 1-continued

Composition of M16 medium

| Component | Concentration | Distributor |
|---|---|---|
| Streptomycin | 50 mg/mL | Manufactured by Thermo Fisher Scientific Inc. (Gibco) |
| Phenol red | 0.01 g/L | manufactured by Wako Pure Chemical Industries, Ltd. |

These components are dissolved in Milli-Q water, then sterilized by filtration through a 0.22 μm filter, and used in culture.

The amount of the agent for improving a normal development rate of a fertilized egg according to the present invention, used in the in vitro development is not particularly limited as long as the amount produces the effect of improving the normal development rate of fertilized eggs. For the addition to an in vitro culture medium for fertilized mammalian eggs, examples of the amount of the agent used can include 0.05 μM to 5 μM, preferably 0.08 μM to 2 μM, more preferably 0.1 μM to 1.5 μM, in terms of the amount of 5-ALA. The dose of the agent for improving a normal development rate of a fertilized egg according to the present invention in the in vivo development is not particularly limited as long as the dose produces the effect of improving the normal development rate of fertilized eggs. The dose is 0.1 to 20 mg/kg/day, preferably 0.5 to 10 mg/kg/day, more preferably 1 to 5 mg/kg/day, in terms of the amount of 5-ALA.

The kit for in vitro development or in vivo development for improving a normal development rate of a fertilized egg according to the present invention is not particularly limited as long as the kit comprises ALAs and an iron compound. A kit further comprising one or more in vitro culture media for fertilized mammalian eggs can be used. The present invention also relates to use of ALAs, preferably ALAs with an iron compound, ALAs and the iron compound with an in vitro culture medium, for preparing an agent for improving a normal development rate of a fertilized egg for in vitro development or in vivo development. The present invention further relates to ALAs, preferably ALAs with an iron compound, ALAs and the iron compound with an in vitro culture medium, for use in improvement in normal development rate of fertilized eggs.

Hereinafter, the present invention will be described more specifically with reference to Examples. However, the technical scope of the present invention is not intended to be limited by these examples.

EXAMPLE 1

[Harvest and In Vitro Culture of Natural Mating-derived Fertilized Eggs—(1)]
(Mating of Mice)

The female mice used to harvest fertilized eggs were female mice of the C57BL/6J lineage (21 weeks old to 27 weeks old, body weight: 21.0 to 24.5 g). The male mice used for mating were male mice of the C57BL/6J lineage (32 to 38 weeks old, body weight: 30.0 to 35.5 g). According to a routine method of controlled ovarian hyperstimulation, 5 U (units) of equine chorionic gonadotropin (serum gonadotrophin) (manufactured by ASKA Pharmaceutical Co., Ltd.) were intraperitoneally administered to each female mouse. 45 to 48 hours later, 5 U (units) of gonadotropin (human chorionic gonadotropin) (manufactured by ASKA Pharmaceutical Co., Ltd.) were intraperitoneally administered to each female mouse. Immediately after the administration of gonadotropin, each female mouse was mated with each male mouse described above.

(Recovery of Fertilized Eggs)

On the next day, the presence or absence of a milky resin-like vaginal plug was determined for the mated female mice, and the oviducts were harvested from the female mice confirmed to have the vaginal plug. The harvested oviducts were left standing in physiological saline (0.9% (w/v) NaCl) for approximately 15 minutes and then transferred into M16 medium supplemented with approximately 300 μg/mL of hyaluronidase (manufactured by Sigma-Aldrich Corp.) for cumulus cell removal treatment. The oviducts were incised, and fertilized eggs were isolated and left standing at 37° C. for 5 to 10 minutes in a $CO_2$ incubator. Then, the fertilized eggs separated from the cumulus cells were recovered and washed with hyaluronidase-unsupplemented M16 medium to remove hyaluronidase. The resulting cumulus cell-free fertilized eggs were left standing at 37° C. in a $CO_2$ incubator.

(In Vitro Culture)

Aside therefrom, a drop of 100 μL of M16 medium covered with mineral oil (manufactured by Sigma-Aldrich Corp.) and supplemented with ALA hydrochloride (manufactured by SBI Pharmaceuticals Co., Ltd.) at a final concentration of 0 μM (control), 0.1 μM, 0.5 μM, or 1 μM was prepared in a 35 mm Petri dish and left standing at 37° C. in a $CO_2$ incubator. 29 or 30 of the cumulus cell-free fertilized eggs were transferred to the resulting drop and cultured in vitro at 37° C. in a $CO_2$ incubator.

(Embryo Development)

After a lapse of 24 hours, 48 hours, 72 hours, and 96 hours from the start of the in vitro culture (0 hours) in the drop, the developmental stage of each embryo was determined by observation under a stereoscopic microscope, and the number of embryos whose development progressed normally and change in development rate were calculated. Specifically, the number of 2-cell eggs 24 hours after the start of the culture, the number of 3-cell, 4-cell, and 8-cell eggs 48 hours thereafter, the number of morulae and blastocysts 72 hours thereafter, and the number of blastocysts 96 hours thereafter were counted as embryos whose development progressed normally at each stage. The number of embryos at each stage is shown in Table 2. The development rate with the number of fertilized eggs (0 hours) defined as 100% is shown in Table 3 and the graph of FIG. 1. For the evaluation of the development rate, the percentage of the number of embryos whose development progressed normally 24 hours, 48 hours, 72 hours, and 96 hours after the start of the culture was calculated with the number of fertilized eggs (0 hours) defined as 100%, and used as a normal development rate. Because of the natural mating, the number of recovered fertilized eggs (0 hours) includes unfertilized eggs to some extent, and there is the possibility that the content of unfertilized eggs varies accidentally among fertilized eggs (0 hours) populations distributed to the respective condition groups even if the fertilized eggs (0 hours) populations have been recovered in the same experiment. The development rate calculated with the number of 2-cell embryos 24 hours postfertilization defined as 100% was calculated in order to eliminate the influence of the content of unfertilized eggs that varies accidentally among the respective condition groups. In short, in order to calculate the development rate on the basis of the number of eggs that reliably started embryo development, the development rate with the number of 2-cell embryos 24 hours postfertilization defined as 100% is shown in Table 4 and the graph of FIG. 2. The results of each test group were statistically analyzed by the square test (chi-square test) with a statistically significant difference of $p<0.01$ (**) and $p<0.05$ (*).

TABLE 2

The number of developed embryos

|  | 0 hr | 24 hr | 48 hr | 72 hr | 96 hr |
|---|---|---|---|---|---|
| Control | 30 | 19 | 18 | 8 | 3 |
| 0.1 µM ALA | 30 | 22 | 19 | 14 | 7 |
| 0.5 µM ALA | 29 | 24 | 21 | 14 | 13 |
| 1 µM ALA | 29 | 19 | 19 | 15 | 13 |

TABLE 3

Change in development rate with the number of fertilized eggs (0 hr) defined as 100%

|  | 0 hr | 24 hr | 48 hr | 72 hr | 96 hr |
|---|---|---|---|---|---|
| Control | 100% | 63% | 60% | 27% | 10% |
| 0.1 µM ALA | 100% | 73% | 63% | 47%* | 23%* |
| 0.5 µM ALA | 100% | 83% | 72% | 48%* | 45%** |
| 1 µM ALA | 100% | 66% | 66% | 52%** | 45%** |

(vs control chi-square test **p < 0.01, *p < 0.05)

<Influence of ALA Addition on Development Rate>

As is evident from Table 2, Table 3, and FIG. 1, when the number of fertilized eggs (0 hours) defined as 100%, the addition of 0.1 µM, 0.5 µM, or 1 µM ALA was confirmed to elevate the development rate as compared with the ALA-unsupplemented control. Particularly, the addition of 0.1 µM ALA offered a development rate of 47% 72 hours postfertilization and a development rate of 23% 96 hours postfertilization, and the addition of 0.5 µM ALA offered a development rate of 48% 72 hours postfertilization. These development rates were significantly higher than the value of the control. Also, the addition of 0.5 µM ALA offered a development rate of 45% 96 hours postfertilization, and the addition of 1 µM ALA offered a development rate of 52% 72 hours postfertilization and a development rate of 45% 96 hours postfertilization. These development rates were remarkably higher than the value of the control.

TABLE 4

Change in development rate with the number of 2-cell embryos 24 hours postfertilization defined as 100%

|  | 24 hr | 48 hr | 72 hr | 96 hr |
|---|---|---|---|---|
| Control | 100% | 95% | 42% | 16% |
| 0.1 µM ALA | 100% | 86% | 64% | 32%* |
| 0.5 µM ALA | 100% | 88% | 58% | 54%** |
| 1 µM ALA | 100% | 100% | 79%** | 68%** |

(vs control chi-square test **p < 0.01, *p < 0.05)

As is evident from Table 4 and FIG. 2, when the number of 2-cell embryos 24 hours postfertilization was defined as 100%, the addition of 0.1 µM, 0.5 µM, or 1 µM ALA was confirmed to elevate the development rate as compared with the ALA-unsupplemented control. Particularly, the addition of 0.1 µM ALA offered a development rate of 32% 96 hours postfertilization. This development rate was significantly higher than the value of the control. The addition of 0.5 µM ALA offered a development rate of 54% 96 hours postfertilization. This development rate was remarkably higher than the value of the control. Also, the addition of 1 µM ALA offered a development rate of 79% 72 hours postfertilization and a development rate of 68% 96 hours postfertilization. These development rates were remarkably higher than the value of the control.

EXAMPLE 2

[Harvest and In Vitro Culture of Natural Mating-derived Fertilized Eggs—(2)]

The study was conducted in the same way as in Example 1 except that: the female mice used to harvest fertilized eggs were female mice of the BDF2 lineage (5 to 24 weeks old, body weight: 16 to 25 g) obtained by the mating between females and males of the BDF1 lineage (F1 of C57BL/6 females×DBA/2 males); the male mice used for mating were male mice of the BDF1 lineage (F1 of C57BL/6 females× DBA/2 males) (46 to 52 weeks old, body weight: 30 to 45 g); and 1 µM ALA was studied. The results are shown in Tables 5 to 7 below and FIGS. 3 and 4.

TABLE 5

The number of developed embryos

|  | 0 hr | 24 hr | 48 hr | 72 hr | 96 hr |
|---|---|---|---|---|---|
| Control | 50 | 42 | 40 | 35 | 34 |
| 1 µM ALA | 50 | 41 | 41 | 40 | 40 |

TABLE 6

Change in development rate with the number of fertilized eggs (0 hr) defined as 100%

|  | 0 hr | 24 hr | 48 hr | 72 hr | 96 hr |
|---|---|---|---|---|---|
| Control | 100% | 84% | 80% | 70% | 68% |
| 1 µM ALA | 100% | 82% | 82% | 80% | 80% |

<Influence of ALA Addition on Development Rate>

As is evident from Table 5, Table 6, and FIG. 3, when the number of fertilized eggs (0 hours) obtained by the mating between the female mice of the BDF2 lineage and the male mice of the BDF1 lineage was defined as 100%, the addition of 1 µM ALA was confirmed to elevate the development rate as compared with the ALA-unsupplemented control.

TABLE 7

Change in development rate with the number of 2-cell embryos 24 hours postfertilization defined as 100%

|  | 24 hr | 48 hr | 72 hr | 96 hr |
|---|---|---|---|---|
| Control | 100% | 95% | 83% | 81% |
| 1 µM ALA | 100% | 100% | 98%** | 98%*** |

(vs control chi-square test **p < 0.01, *p < 0.05)

As is evident from Table 7 and FIG. 4, when the number of 2-cell embryos 24 hours postfertilization was defined as 100%, the addition of 1 µM ALA was confirmed to elevate the development rate as compared with the ALA-unsupplemented control. Particularly, the addition of 1 µM ALA offered a development rate of 98% 72 hours and 96 hours postfertilization. This development rate was remarkably higher than the value of the control.

Next, the embryo development-promoting effect of ALA on low-temperature culture was examined in an in vitro culture system of fertilized eggs of C57BL/6J mice obtained by natural mating and in vitro fertilization.

EXAMPLE 3

[Harvest and In Vitro Culture of Natural Mating-derived Fertilized Eggs—(3)]

According to a routine method of controlled ovarian hyperstimulation, 5 U (units) of equine chorionic gonadotropin (serum gonadotropin) (ASKA Pharmaceutical Co., Ltd.) were intraperitoneally administered to each female mouse of the C57BL/6J lineage (4 weeks old to 6 weeks old). 45 to 48 hours later, 5 U (units) of gonadotropin (human chorionic gonadotropin) (ASKA Pharmaceutical Co., Ltd.) were intraperitoneally administered thereto. Immediately after the administration of gonadotropin, each female mouse was mated with each male mouse of the C57BL/6J lineage. In the next morning, the oviducts were recovered into physiological saline (0.9% (w/v) NaCl) from the female mice that were able to be confirmed to have a vaginal plug. The oviducts were perfused with KSOM or mWM (both were purchased from ARK Resource Co., Ltd., http://www.ark-resource.co.jp/seihin/cryopreservation-liq-uid/) containing hyaluronidase (approximately 300 μg/ml, Sigma-Aldrich Corp.). After removal of cumulus cells from the obtained fertilized eggs, the fertilized eggs were recovered. In order to remove hyaluronidase, the fertilized eggs were washed with each medium (KSOM or mWM) and maintained in KSOM or mWM (ARK Resource Co., Ltd.) in an incubator of 37° C. and 5% $CO_2$ until the fertilized eggs were recovered from all of the female mice. These two media used are typical media for use in mouse embryo culture. KSOM is a typical low glucose-containing medium, whereas mWM is a high glucose-containing medium.

20 to 50 of the recovered fertilized eggs were transferred into a drop (covered with mineral oil (Sigma-Aldrich Corp.)) consisting of 100 μl of ALA-unsupplemented or ALA-supplemented (1 μM or 3 μM) medium (KSOM or mWM). Subsequently, the fertilized eggs were cultured under two culture conditions: a condition of 37° C. and 5% $CO_2$ and a condition of 35° C. and 5% $CO_2$. The number of 2-cell eggs was counted 24 hours after the fertilized egg harvest, and the number of blastocysts was counted 96 hours thereafter. The development rate was evaluated in the same way as in Example 1. The results about KSOM are shown in Tables 8 to 10 and FIGS. 5 and 6. The results about mWM are shown in Tables 11 to 13 and FIGS. 7 and 8.

TABLE 8

The number of developed embryos in KSOM

|  | 0 hr | 24 hr | 48 hr | 96 hr |
| --- | --- | --- | --- | --- |
| 37° C. control | 39 | 16 | 15 | 9 |
| 35° C. control | 54 | 33 | 21 | 2 |
| 35° C. 1 μM ALA | 58 | 39 | 23 | 6 |

TABLE 9

Change in development rate with the number of fertilized eggs (0 hr) in KSOM defined as 100%

|  | 0 hr | 24 hr | 48 hr | 96 hr |
| --- | --- | --- | --- | --- |
| 37° C. control | 100% | 41% | 38% | 23% |
| 35° C. control | 100% | 61% | 39% | 4% |
| 35° C. 1 μM ALA | 100% | 67% | 40% | 10% |

TABLE 10

Change in development rate with the number of 2-cell embryos 24 hours postfertilization in KSOM defined as 100%

|  | 24 hr | 48 hr | 96 hr |
| --- | --- | --- | --- |
| 37° C. control | 100% | 94% | 56% |
| 35° C. control | 100% | 64% | 6% |
| 35° C. 1 μM ALA | 100% | 59% | 15% |

TABLE 11

The number of developed embryos in mWM

|  | 0 hr | 24 hr | 48 hr | 96 hr |
| --- | --- | --- | --- | --- |
| 37° C. control | 113 | 55 | 49 | 39 |
| 35° C. control | 123 | 57 | 47 | 28 |
| 35° C. 1 μM ALA | 122 | 59 | 48 | 27 |
| 35° C. 3 μM ALA | 125 | 62 | 62 | 40 |

TABLE 12

Change in development rate with the number of fertilized eggs (0 hr) in mWM defined as 100%

|  | 0 hr | 24 hr | 48 hr | 96 hr |
| --- | --- | --- | --- | --- |
| 37° C. control | 100% | 49% | 43% | 35% |
| 35° C. control | 100% | 46% | 38% | 23% |
| 35° C. 1 μM ALA | 100% | 50% | 39% | 22% |
| 35° C. 3 μM ALA | 100% | 50% | 50% | 32% |

TABLE 13

Change in development rate with the number of 2-cell embryos 24 hours postfertilization in mWM defined as 100%

|  | 24 hr | 48 hr | 96 hr |
| --- | --- | --- | --- |
| 37° C. control | 100% | 89% | 71% |
| 35° C. control | 100% | 82% | 49% |
| 35° C. 1 μM ALA | 100% | 81% | 46% |
| 35° C. 3 μM ALA | 100% | 100% | 65% |

<Influence Under Low-temperature (35° C.) Culture Condition on Development Rate>

In the comparison of the development rate between the 37° C. culture and the 35° C. culture of the ALA-unsupplemented group (control), in the case of using KSOM (Table 9/FIG. 5 and Table 10/FIG. 6), the development rate to blastocysts 96 hours after the start of the culture was significantly decreased from 23% to 4% when the number of fertilized eggs (0 hours) was defined as 100% (Table 9) and from 56% to 6% when the number of 2-cell embryos 24 hours postfertilization was defined as 100% (Table 10). In the case of using mWM (Table 12/FIG. 7 and Table 13/FIG. 8) as well, the development rate was significantly decreased from 35% to 23% when the number of fertilized eggs (0 hours) was defined as 100% (Table 12) and from 71% to 49% when the number of 2-cell embryos 24 hours postfertilization was defined as 100% (Table 13). These results demonstrated that the low-temperature culture of C57BL/6J fertilized eggs under the present experimental conditions impairs progress in development.

<Influence of ALA Addition Under Low-temperature (35° C.) Culture Condition on Development Rate>

Under the 35° C. culture condition, in the case of using KSOM, the development rate to blastocysts 96 hours after the start of the culture in the ALA-unsupplemented group (control) was 4% when the number of fertilized eggs (0 hours) was defined as 100% (Table 9) and was 6% when the number of 2-cell embryos 24 hours postfertilization was defined as 100% (Table 10). By contrast, the development rate of the 1 µM ALA-supplemented group was significantly elevated to 10% when the number of fertilized eggs (0 hours) was defined as 100% (Table 9) and to 15% when the number of 2-cell embryos 24 hours postfertilization was defined as 100% (Table 10). On the other hand, in the case of using mWM, the development rate to blastocysts 96 hours after the start of the culture in the ALA-unsupplemented group (control) was 23% when the number of fertilized eggs (0 hours) was defined as 100% (Table 12) and was 49% when the number of 2-cell embryos 24 hours postfertilization was defined as 100% (Table 13). By contrast, the development rate of the 3 µM ALA-supplemented group was significantly elevated to 32% when the number of fertilized eggs (0 hours) was defined as 100% (Table 12) and to 65% when the number of 2-cell embryos 24 hours postfertilization was defined as 100% (Table 13). Unlike KSOM, no significant elevation was found in the development rate of the 1 µM ALA-supplemented group (Tables 12 and 13).

EXAMPLE 4

[Harvest and In Vitro Culture of In Vitro Fertilization-derived Fertilized Eggs]

5 U (units) of equine chorionic gonadotropin (serum gonadotropin) (ASKA Pharmaceutical Co., Ltd.) were intraperitoneally administered to each female mouse of the C57BL/6J lineage (3.9 weeks old to 4.0 weeks old). 45 to hours later, 5 U (units) of gonadotropin (human chorionic gonadotropin) (ASKA Pharmaceutical Co., Ltd.) were intraperitoneally administered thereto for controlled ovarian hyperstimulation. 15 hours after the administration of gonadotropin, the oviducts were recovered by opening the abdomens. In mineral oil, the ampullae of the oviducts were incised with a dissecting needle, and the ova were recovered into a drop of mHTF medium (ARK Resource Co., Ltd.). Sperms were recovered from the cauda epididymides of C57BL/6J male mice and cultured in mHTF medium at 37° C. for 40 minutes to 1 hour under 5% $CO_2$ conditions for capacitation. 2 µl to 4 µl of the mHTF medium containing the sperms was added to the medium drop containing the recovered ova for insemination, and cultured at 37° C. under 5% $CO_2$ conditions. 4 hours to 6 hours after the insemination, the fertilized eggs were washed with KSOM (ARK Resource Co., Ltd.) or mWM (ARK Resource Co., Ltd.) to remove cumulus cells and sperms. The fertilized eggs were temporarily cultured in KSOM or mWM in an incubator of 37° C. and 5% $CO_2$ until all of the fertilized eggs were recovered.

25 of the fertilized eggs per drop were transferred to a drop (covered with mineral oil (Sigma-Aldrich Corp.)) consisting of 100 µl of ALA-unsupplemented or ALA-supplemented (1 µM or 3 µM) medium (KSOM or mWM). Subsequently, the fertilized eggs were cultured under three conditions: a condition of 37° C. and 5% $CO_2$, a condition of 35° C. and 5% $CO_2$, and a condition of 35.5° C. and 5% $CO_2$. The number of 2-cell eggs was counted 24 hours after the ovum recovery, and the number of blastocysts was counted 96 hours thereafter. Since the development of fertilized eggs obtained by in vitro fertilization is slightly slow, the number of blastocysts was also counted 120 hours after the ovum recovery. The development rate of embryos at each culture time was calculated on the basis of the number of 2-cell embryos 24 hours postfertilization defined as 100%. The results about KSOM are shown in Tables 14 and 15 and FIGS. 9 and 11. The results about mWM are shown in Tables 16 and 17 and FIGS. 10, 12, and 13.

TABLE 14

The number of developed embryos in KSOM

|  | 0 hr | 24 hr | 48 hr | 72 hr | 120 hr |
|---|---|---|---|---|---|
| 37° C. control | 100 | 72 | 62 | 59 | 53 |
| 35.5° C. control | 100 | 64 | 33 | 32 | 26 |
| 35° C. control | 100 | 74 | 31 | 28 | 18 |
| 35° C. 1 µM ALA | 100 | 61 | 27 | 26 | 22 |
| 35° C. 3 µM ALA | 100 | 60 | 29 | 27 | 16 |

TABLE 15

Change in development rate with the number of 2-cell embryos 24 hours postfertilization in KSOM defined as 100%

|  | 24 hr | 48 hr | 72 hr | 120 hr |
|---|---|---|---|---|
| 37° C. control | 100% | 86% | 82% | 74% |
| 35.5° C. control | 100% | 52% | 50% | 41% |
| 35° C. control | 100% | 42% | 38% | 24% |
| 35° C. 1 µM ALA | 100% | 44% | 43% | 36% |
| 35° C. 3 µM ALA | 100% | 48% | 45% | 27% |

TABLE 16

The number of developed embryos in mWM

|  | 0 hr | 24 hr | 48 hr | 72 hr | 96 hr |
|---|---|---|---|---|---|
| 37° C. control | 100 | 65 | 69 | 61 | 57 |
| 35.5° C. control | 101 | 58 | 55 | 47 | 31 |
| 35.5° C. 1 µM ALA | 103 | 60 | 60 | 49 | 42 |
| 35.5° C. 3 µM ALA | 101 | 52 | 52 | 46 | 39 |
| 35° C. control | 101 | 56 | 55 | 34 | 14 |
| 35° C. 1 µM ALA | 100 | 51 | 55 | 46 | 29 |
| 35° C. 3 µM ALA | 100 | 52 | 44 | 27 | 20 |

TABLE 17

Change in development rate with the number of 2-cell embryos 24 hours postfertilization in mWM defined as 100%

|  | 24 hr | 48 hr | 72 hr | 96 hr |
|---|---|---|---|---|
| 37° C. control | 100% | 106% | 94% | 83% |
| 35.5° C. control | 100% | 95% | 81% | 53% |
| 35.5° C. 1 µM ALA | 100% | 100% | 82% | 70% |
| 35.5° C. 3 µM ALA | 100% | 100% | 88% | 75% |
| 35° C. control | 100% | 98% | 61% | 25% |
| 35° C. 1 µM ALA | 100% | 108% | 90% | 53% |
| 35° C. 3 µM ALA | 100% | 85% | 52% | 38% |

<Influence Under Low-temperature (35° C. and 35.5° C.) Culture Condition on Development Rate>

In the comparison of the development rate among the 37° C. culture, 35.5° C. culture, and the 35° C. culture of the ALA-unsupplemented group (control), in the case of using KSOM (Table 15 and FIG. 9), the development rate to blastocysts 120 hours after the start of the culture was significantly decreased from 74% at 37° C. to 41% at 35.5° C. and 24% at 35° C. when the number of 2-cell embryos 24 hours postfertilization was defined as 100%. In the case of using mWM (Table 17 and FIG. 10) as well, the development rate to blastocysts 96 hours after the start of the culture was significantly decreased in a temperature-dependent manner from 83% at 37° C. to 53% at 35.5° C. and 25% at 35° C. when the number of 2-cell embryos hours postfertilization was defined as 100%. These results demonstrated that the low-temperature culture of C57BL/6J in vitro fertilized eggs under the present experimental conditions inhibits progress in development, as with the fertilized eggs obtained by natural mating.

<Influence of ALA Addition Under Low-temperature (35° C. and 35.5° C.) Culture Condition on Development Rate>

In the case of using KSOM (Tables 14 and 15), under the 35° C. culture condition (FIG. 11), the development rate to blastocysts 120 hours after the start of the culture in the ALA-unsupplemented group was 24% when the number of 2-cell embryos 24 hours postfertilization was defined as 100%. By contrast, the development rate was 36% in the 1 µM ALA-supplemented group and 27% in the 3 µM ALA-supplemented group. Thus, the addition of 1 µM ALA in the 35° C. culture significantly elevated the development rate to blastocysts.

In the case of using mWM (Tables 16 and 17), under the 35.5° C. culture condition (FIG. 12), the development rate to blastocysts 96 hours after the start of the culture in the ALA-unsupplemented group was 53% when the number of 2-cell embryos 24 hours postfertilization was defined as 100%. By contrast, the development rate was 70% in the 1 µM ALA-supplemented group and 75% in the 3 µM ALA-supplemented group. Thus, the addition of ALA significantly elevated the development rate to blastocysts. Under the 35° C. culture condition (FIG. 13) as well, the development rate to blastocysts 96 hours after the start of the culture in the ALA-unsupplemented group was 25% when the number of 2-cell embryos 24 hours postfertilization was defined as 100%. By contrast, the development rate was 53% in the 1 µM ALA-supplemented group and 38% in the 3 µM ALA-supplemented group. Thus, the addition of 1 µM ALA in the 35° C. culture significantly elevated the development rate to blastocysts.

(Discussion)

<Influence of ALA on Development Rate>

For fertilized eggs or embryos whose development does not normally progress, it is thought that reduction in the amount of intracellular heme synthesized, i.e., insufficient supply of endogenous 5-ALA, induces disorder of energy production and thereby arrests early development. It is thought that the replenishment of 5-ALA and further, iron can enhance a development rate or a conception rate.

<Influence of Low-temperature Culture on Embryo Development>

In an in vitro development system of C57/BL6 fertilized eggs obtained both from natural mating and from in vitro fertilization, reduction in development rate to blastocysts and inhibition of development were found in the low-temperature culture at 35.5° C. and 35° C. as compared with the normal culture at 37° C. Particularly, in the embryo culture of the in vitro fertilized eggs, temperature-dependent inhibition of development into blastocysts was observed (FIGS. 9 and 10), indicating that this system can serve as a model of infertility caused by hypothermia.

<Embryo Development-promoting Effect of ALA Under Low-temperature Culture Condition>

The effect of ALA on mouse embryo development in low-temperature culture was studied under the present experimental conditions. As a result, ALA was confirmed to exhibit a development-promoting effect in low-temperature culture for the in vitro development of fertilized eggs obtained by natural mating and in vitro fertilized eggs. Particularly, in the case of using mWM, a strong promoting effect was observed. mWM is a high-glucose medium, whereas KSOM is a low-glucose medium, suggesting the possibility that the effect of ALA is glucose-dependent.

<Potential of ALA as Therapeutic Drug for Human Infertility>

The present experiments employed fertilized mouse eggs. The development of fertilized eggs at low temperatures is presumably a status under stress similar to hypothermia, which is a possible cause of infertility. Thus, the possibility was shown that the dosing of ALA is effective for the amelioration of human infertility caused by hypothermia.

INDUSTRIAL APPLICABILITY

The present invention can enhance the efficiency of preparation of embryos suitable for embryo transfer to the mother from fertilized eggs and is therefore useful in the fields of animal industry and infertility treatment.

The invention claimed is:

1. A method for improving a development rate of a fertilized egg, consisting essentially of contacting the fertilized egg with a compound represented by the following formula (I) or a salt thereof between fertilization and blastocyst formation:

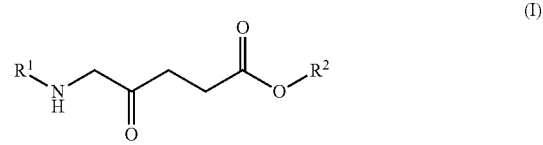

wherein $R^1$ and $R^2$ represent a hydrogen atom.

2. The method for improving a development rate of a fertilized egg according to claim 1, wherein an iron compound is used in combination with the compound represented by formula (I) or a salt thereof.

3. The method for improving a development rate of a fertilized egg according to claim 2, wherein the iron compound is one or more compounds selected from ferric chloride, iron sesquioxide, iron sulfate, ferrous pyrophosphate, ferrous citrate, iron sodium citrate, sodium ferrous citrate, iron ammonium citrate, ferric pyrophosphate, iron lactate, ferrous gluconate, iron sodium diethylenetriaminepentaacetate, iron ammonium diethylenetriaminepentaacetate, iron sodium ethylenediaminetetraacetate, iron ammonium ethylenediaminetetraacetate, iron sodium dicarboxymethylglutamate, iron ammonium dicarboxymethylglutamate, ferrous fumarate, iron acetate, iron oxalate, ferrous succinate, sodium iron succinate citrate, heme iron, iron dextran, iron triethylenetetramine, lactoferrin iron, transferrin iron, sodium iron chlorophyllin, ferritin iron, saccharated iron oxide, and iron glycine sulfide.

4. The method for improving a development rate of a fertilized egg according to claim 1, wherein the fertilized egg is a fertilized egg obtained by in vitro fertilization or in vivo fertilization.

5. The method for improving a development rate of a fertilized egg according to claim 1, wherein a medium for improvement in fertilized egg development rate comprising an in vitro culture medium for fertilized mammalian eggs and the compound represented by formula (I) or a salt thereof is used.

6. A method for improving a development rate of a fertilized egg, consisting essentially of administering to a female parent subject a compound represented by the following formula (I) or a salt thereof between fertilization and blastocyst formation:

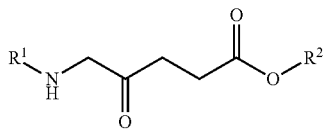

wherein $R^1$ and $R^2$ represent a hydrogen atom.

7. The method for improving a development rate of a fertilized egg according to claim 6, wherein an iron compound is used in combination with the compound represented by formula (I) or a salt thereof.

8. The method for improving a development rate of a fertilized egg according to claim 7, wherein the iron compound is one or more compounds selected from ferric chloride, iron sesquioxide, iron sulfate, ferrous pyrophosphate, ferrous citrate, iron sodium citrate, sodium ferrous citrate, iron ammonium citrate, ferric pyrophosphate, iron lactate, ferrous gluconate, iron sodium diethylenetriaminepentaacetate, iron ammonium diethylenetriaminepentaacetate, iron sodium ethylenediaminetetraacetate, iron ammonium ethylenediaminetetraacetate, iron sodium dicarboxymethylglutamate, iron ammonium dicarboxymethylglutamate, ferrous fumarate, iron acetate, iron oxalate, ferrous succinate, sodium iron succinate citrate, heme iron, iron dextran, iron triethylenetetramine, lactoferrin iron, transferrin iron, sodium iron chlorophyllin, ferritin iron, saccharated iron oxide, and iron glycine sulfide.

9. The method for improving a development rate of a fertilized egg according to claim 6, wherein the fertilized egg is a fertilized egg obtained by in vitro fertilization or in vivo fertilization.

10. The method for improving a development rate of a fertilized egg according to claim 7, wherein the fertilized egg is a fertilized egg obtained by in vitro fertilization or in vivo fertilization.

* * * * *